United States Patent

Re et al.

[11] Patent Number: 5,109,103
[45] Date of Patent: Apr. 28, 1992

[54] FLUORINATED POLYESTERS

[75] Inventors: Alberto Re, Milan; Marco De Giorgi, Varese; Gerardo Caporiccio, Milan, all of Italy

[73] Assignee: Ausimont S.p.A., Milan, Italy

[21] Appl. No.: 667,214

[22] PCT Filed: Dec. 5, 1986

[86] PCT No.: PCT/EP86/00712
§ 371 Date: Jul. 22, 1987
§ 102(e) Date: Jul. 22, 1987

[87] PCT Pub. No.: WO87/03608
PCT Pub. Date: Jun. 18, 1987

Related U.S. Application Data

[63] Continuation of Ser. No. 403,071, Sep. 5, 1989, abandoned, which is a continuation of Ser. No. 93,749, Jul. 22, 1987, abandoned.

[30] Foreign Application Priority Data

Dec. 5, 1985 [IT] Italy ................. 23112 A/85

[51] Int. Cl.$^5$ .......................................... C08G 63/682
[52] U.S. Cl. ..................... 528/272; 528/300; 528/308.1; 528/308.7; 528/361; 528/401; 528/425; 525/418; 525/437
[58] Field of Search ............ 528/272, 300, 308.1, 528/308.7, 361, 401, 425; 525/418, 437

[56] References Cited

U.S. PATENT DOCUMENTS 3,810,874  5/1974  Mitsch et al. ................. 528/70
3,847,978  11/1974 Sianesi et al. ................ 562/577
4,523,039  6/1985  Lagow et al. ................. 568/615

Primary Examiner—John Kight, III
Assistant Examiner—S. A. Acquah
Attorney, Agent, or Firm—Morgan & Finnegan

[57] ABSTRACT

New polyesters comprising polyoxyfluoroalkylene blocks are prepared by polycondensation of diols with dicarboxylic acids or with derivatives thereof, said fluorinated polyesters being characterized by such improved surface properties that any subsequent treatments of the surface of the articles obtained therefrom are needless.

10 Claims, No Drawings

FLUORINATED POLYESTERS

This is a continuation of co-pending application Ser. No. 07/403,071, filed on Sep. 5, 1989, now abandoned, which is a continuation application of Ser. No. 07/093,749 filed Jul. 22, 1987, now abandoned.

FIELD OF THE INVENTION

The present invention relates to fluorinated polyesters of the thermoplastic or thermoelastomeric type.

BACKGROUND OF THE INVENTION

There are known thermoplastic polyesters, which are widely utilized as films, fibers, supports for magnetic tapes, structural materials infields such as the electronic or the biomedical. They are generally prepared by polycondensation of aromatic diacides or their derivatives with diols. Typical examples are polyethyleneterephthalate and polybutyleneterephthalate, which are obtained by polycondensation of terephthalic acid or a of a derivative thereof, for example a diester, with ethylene glycol or butandiol, respectively.

There are also known thermoelastomeric polyesters obtained by condensation of a diacid or a derivative thereof, such as e.g. a diester, with a low molecular weight glycol and with a polyglycol, generally a polyoxyalkylene glycol having a molecular weight from 1000 to 3000.

The thermoplastic and thermoelastomeric polyesters are characterized by high mechanical and electrical characteristics, a good stability to solvents and to hydrolysis.

For a plurality of uses such as films, supports for magnetic tapes, fibers, in various sectors of goods, they exhibit however considerable drawbacks, as they have a low oil and water-repellency, a low resistance to soiling and low free flowing properties, characterized by a high friction coefficient, so that a subsequent finishing treatment of such articles is absolutely necessary.

In particular, as regards the use for magnetic recording tapes, where the material flows on metal or plastic surfaces, a surface treatment of said surface with a lubricant is required in order to reduce friction and to secure the sliding of the tape and preserve it as much as possible from the wearing. For these uses, very thin layers on the substrate surface, generally from 50 to 1,000 Å, are sufficient.

For other uses, for example in particular in the biomedical field, the conventional hydrogenated polyesters, although exhibiting - in comparison with other utilizable materials - improved impermeability and mechanical properties, do not exhibit good biocompatiblity and antithrombogenicity.

With a view to overcoming these drawbacks, the hydrogenated polyesters are therefore subjected to finishing processes or surface treatments.

These finishing processes or these surface treatments are generally carried out, for example, with a fluorinated diol or with a solution or a dispersion of a fluorinated plastic polymer, such as, for example, a polytetrafluoroethylene dispersion, depending on the type of application. However, these fluorinated coatings exhibit the drawback of not sufficiently adhering to the substrate, owing to the surface properties which are typical of the fluorinated polymer and which interfere with the adhesion. By consequence, since it is not possible to maintain the fluorinated layer adherent to the article for a sufficiently long period of time, a degradation of the surface properties occurs, such as resistance to chemical agents, oil- and water-repellency, resistance to soiling, free flowing which, conversely, are indispensable for a plurality of uses.

An alternative method of increasing the duration of the above said surface properties consists in chemically binding a fluorinated monomer to the polymeric substrate by grafting. This process can be carried out, for example, by using radiation or electric discharge.

With such method, however, the attainment of a uniform layer is strictly related to the substrate nature. In fact, on substrates having an irregular shape no uniform layer of fluorinated coating can be obtained.

According to another method of obtaining fluorinated coatings on non-fluorinated polyesters, a non-fluorinated polyester is coextruded with a fluorinated copolymer, for example a tetrafluoroethylene/hexafluoropropene polymer. This method, however, besides requiring a particularly complex technology, can be rarely used, as it can be applied only for particular types of articles, for example fibers.

By consequence, there was the requirement of having available readily processable polyesters which permit to overcome the above-said problems of finishing or of surface treatment, and at the same time having the above-cited characteristics of chemical inertia, mechanical properties, oil- and water-repellency, biocompatiblity.

THE PRESENT INVENTION

It has now surprisingly been found that polyesters comprising fluoropolyoxyalkylene units represent a novel technological solution which permits to overcome the above-cited limitations as they permit to avoid all surface treatments or finishing operations.

Thus, the object of the present invention is a polyester characterized by a block structure and comprising, with respect to the total number of moles constituting the polyester, amounts not higher than 45% by moles of at least one fluoropolyoxyalkylene comprising the repeating fluoropolyoxyalkylene units selected from the following classes:

I $(C_2F_4O)$, $(CF_2O)$, said units being randomly distributed along the fluoropolyoxyalkylene chain;

II $(C_3F_6O)$, $(C_2F_4O)$, $(CFXO)$ where $X=-F$ or $-CF_3$, said units being randomly distributed along the perfluoropolyoxyalkylene chain;

III $-CH_2-CF_2-CF_2-O-$ said units being linked to one another inside the fluoropolyoxyalkylene chain as shown by the following structural formula: $-(O-CF_2-CF_2-CH_2)_p-O-R'_f-O-(CH_2-CF_2-CF_2-O)_q-$ where $R'_f$ is a fluoroalkylene group, preferably containing 1 to 8 carbon atoms, p and q are integers, $p+q$ is at least 2 and, preferably, up to 200;

IV

said units being linked to one another inside the fluoropolyoxyalkylene chain as shown by the following structural formula:

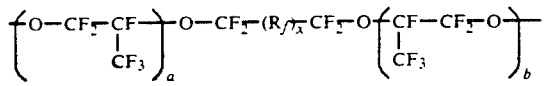

where $R_f$ is a fluoroalkylene group, preferably containing 1 to 8 carbon atoms, x is 0 or 1, a and b are integers and a+b is at least 2 and, preferably, up to 30;

V $(CF_2CF_2O)$;
VI $(CF_2CF_2CF_2O)$.

The fluorinated polyesters of the invention are prepared by directly carrying out a polycondensation of fluoropolyalkylenes comprising the above said repeating units with the cited diols or carboxylic diacids or derivatives thereof. Such fluoropolyoxyalkylenes having functional groups at both ends contain hydroxy end groups or carboxylic end groups and have an average molecular weight of from about 400 to 10,000, the minimum value depending on the type of repeating structure, so that polyesters having a molecular weight equal to at least 20,000 are obtained.

The polymers so obtained, besides retaining the excellent properties of the polyesters, particularly mechanical and electrical properties, chemical inertia to common solvents, exhibit also improved surface characteristics, such as oil- and water-repellency, low friction coefficient, chemical inertia to aggressive agents such as hydrocarbon fluids or chlorinated solvents, so avoiding the difficulties connected with the preparation and the carrying out of the fluorinated surface treatment needed for the conventional polyesters. These materials are therefore particularly suitable for a wide variety of uses such as e.g. oil- and water-repellent films and fibers, substrates for magnetic tapes, biocompatible structural materials for biomedical uss.

For the preparation of the polyesters of the invention the following compounds are utilized:

1) a hydrogenated diacid or diester or diacylchloride having the following general formula:

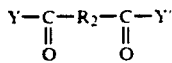

wherein Y and Y', equal or different one another, are halogen or OR', wherein R' is H or an alkyl radical containing from 1 to 8 carbon atoms or an aryl radical having from 6 to 10 carbon atoms;

$R_2$ is a divalent radical having from 2 to 30 carbon atoms such as, for example:

a) an alkylene radical of the type:

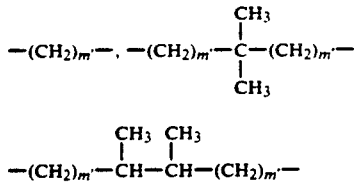

wherein m' is an integer from 2 to 20;

b) a fluorinated or non-fluorinated arylene radical such as for example para- or meta-phenylene, para- or meta-xylene;

c) a cycloaliphatic or polycyclic, fluorinated or non-fluorinated, divalent radical, such as for example 1,4-cyclohexylene, 1,3-cyclohexylene, 2-methyl-1,4-cyclohexylene, 2-methyl-1,3-cyclohexylene, diarylenemethane. etc.

Particularly suitable for the purposes of the invention are the aromatic dicarboxylic acids, such as for example the terephthalic, phthalic and isophthalic acids and their derivatives;

2) a hydrogenated diol containing an alkylene radical having from 2 to 14 carbon atoms, such as ethylene, propylene, tetremethylene, hexamethylene, dodecmethylene, cyclohexylene, 2,2-dimethyltrimethylene or cyclohexan-dimethylene;

3) a difunctional derivative having an average molecular weight from about 400 to 10,000, preferably from 500 to 5,000, comprising the fluoropolyoxyalkylene units described above in classes I, II, III, IV, V and VI and having end groups of the following type:

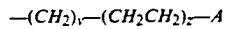

wherein v and z are integers or zero, preferably v is 0 or 1, and z is 0 or an integer up to 3;

A is OH, in such case v being at least 1, or COY, Y being the same as defined before.

Difunctional derivatives having end groups as described before and belonging to class I are particularly selected from those comprised in the following general formula:

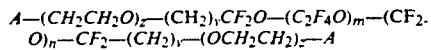

wherein v, z and A have the meaning defined hereinbefore and m and n are positive integers such that the molecular weight falls within the indicated range.

one can prepare these fluoropolyoxyalkylene derivatives according to known methods, as described for example in U.S. Pat. No. 3,810,874 and U.S. Pat. No. 3,847,978.

Difunctional derivatives having the above described end groups and belonging to class II are particularly selected from those comprised in following general formula:

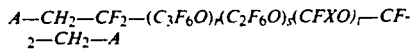

wherein X is —F or —$CF_3$, indexes r, s, t are positive integers such that the molecular weight is as above indicated, and A is as defined hereinbefore.

One can prepare such compounds by photo-oxidation of $C_3F_6$ and $C_2F_4$ mixtures, as described in U.S. Pat. No. 3,665,041, and by successively converting —COF end groups into groups containing the end group A, such conversion being accomplished according to known methods as described for example in U.S. Pat. No. 3,847,978 and U.S. Pat. No. 3,810,874.

Difunctional derivatives having the above described end groups and belonging to class III are particularly selected from those comprised in following general formula:

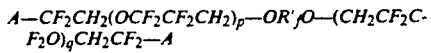

wherein p, q, A and $R'_f$ are the same as defined hereinabove.

These compounds are described in published European patent application No. 148,482 and the end groups containing —COF can be converted so as to have end groups A, as is described in U.S. Pat. No. 3,847,978 and U.S. Pat. No. 3,810,874.

Difunctional derivatives having the above described end groups and belonging to class IV are particularly selected from those comprised in following general formula:

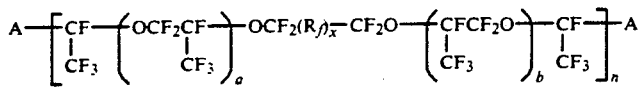

where a, b, A, $R_f$, x have the meaning defined hereinbefore, n is a positive integer.

Such compounds are described in published European patent application No. 151,877 and the end groups containing —COF are converted in order to have end groups A as is described in U.S. Pat. No. 3,847,978 and U.S. Pat. No. 3,810,874.

Difunctional derivatives having end groups as described before and belonging to classes V and VI, are prepared by the processes described respectively in U.S. Pat. No. 4,523,039 and European patent application No. 148,482, both successively followed by the treatments described in Italian patent application No. 22920 A/85;

4) a hydrogenated polyoxyalkylene glycol having an average molecular weight from about 400 to 4,000 and preferably from 1,000 to 2,000, having the following general formula:

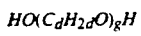

where $d = 1-4$ and $g = 6-70$, $C_dH_{2d}$ being linear or having side-chains.

Representative examples of such class of compounds are: polyethylene glycol, polypropylene glycol, polytetramethylene glycol.

The fluorinated polyester of the present invention are prepared by properly mixing the above-specified compounds in such way that at least one of them is a fluoropolyoxyalkylene derivative and the molecular weight of the final polyester is not lower than 20,000.

According to the present invention, the fluorinated polyesters comprising the fluoropolyoxyalkylene derivative in amounts not exceeding 5% by moles, preferably from 0.1% to 5% by moles with respect to the total number of moles consisting the polyester are particularly suitable for substrates for magnetic tapes, oil- and water-repellent films and fibers.

The polyesters of the invention having a content of fluoropolyoxyalkylene units higher than 5% by moles are particularly utilizable in the biomedical field due to their high biocompatiblity.

By properly varying the components from 1) to 4), it is possible to obtain thermoplastic or thermoplastic materials. The thermoelastomeric materials contain a rubber-like phase which may consist either of fluoropolyoxyalkylene or of polyoxyalkylene glycol or of mixtures thereof. Generally, in the presence of high fluoropolyoxyalkylene contents, for example of 30% by moles, the polyester is thermoelastomeric; in case of lower amounts, $\leq 5\%$ by moles, it is necessary to add polyoxyalkylene glycols.

One can prepare the polyesters of the invention by conventional polycondensation techniques, such as for example, in bulk, in solution, in emulsion, interface polycondensation.

Always according to the known polyester synthesis methods, the polycondensation can be carried out starting from dicarboxylic acids and diols, or by transesterification starting from diesters and diols, or from diacylchlorides and diols.

Particularly suitable for the purposes of the present invention is the transesterification and bulk-polycondensation process starring from mixtures of diesters and diols.

Such process is accomplished by first heating the mixture of reagents diesters and diols, in proper molar ratios, in the presence of a catalyst, to a temperature from about 200° C. to 240° C.; in this step, the distillation of the by-products (alcohols) generated during the transesterification takes place.

The reaction is carried out in an inert atmosphere, under vigorous stirring and for a time sufficient for the complete removal of the by-products.

The operation time depends on the monomer type, the temperature, the catalyst and the excess of diol employed.

This process step leads to a low molecular weight prepolymer which is converted to a polymer having a molecular weight suitable for high temperature (250° C.-300° C.) polycondensation under stirring and at a residual pressure lower than 1 torr, in order to remove the excess of the low molecular weight diol.

The polycondensation time, which is a function of the operative conditions, generally ranges from 0.5 to 10 hours.

It is possible to use different types of catalysts, such as, for example, salts of divalent and trivalent metals, such as calcium, manganese, iron, magnesium, aluminum, zinc; oxides of germanium, lead and antimony; alkaline metals (sodium, potassium) alkoxides, titanium alkoxides (isopropylate, butylate).

Both process steps, i.e. transesterification and polycondensation, are generally effected in the absence of solvents: the materials are in the molten state.

The polycondensation can be also carried out in solution, using diacylchlorides and diols.

The fluorinated polyesters of the present invention, as mentioned above, permit to obtain, by suitably varying the starring composition of the mixture, both plastic-type and elastomeric-type materials, each type being characterized by excellent mechanical properties. Those skilled in the art will have no difficulty in determining the best compositions for the various utilizations.

The mechanical properties of these fluorinated polyesters, however, can be modified, according to the requirements and the desired appliances, by adding various inorganic additives known in the art, such as carbon black, silica gel, alumina and glass fibers. For a few uses, in particular, it is advisable to incorporate stabilizers to heat and to ultraviolet radiations, well known in the art.

Furthermore, it is possible to obtain polyesters with a different fluorine content by properly varying the initial molar ratio of the fluoropolyoxyalkylene derivative to other reagents.

The fluorinated polyesters obtained according to the present invention have the same fields of use as the analogous non-fluorinated polyesters with the advantage that the articles prepared from said fluorinated polyesters, for example, by injection molding or compression molding processes, exhibit, as compared with the known products, improved properties as regards oil- and water-repellency, self-lubrication, free flowing and biocompatiblity.

This properties improvement occurs also for very low amounts, even of 0.5% by moles, of fluoropolyoxyalkylene compound with respect to the final polyester.

A further advantage of the polyesters of the present invention is the possibility of mixing a thermoplastic or thermoelastomeric polyester having a high fluorine content, according to the invention, with other fluorinated or non-fluorinated polymeric materials, and of treating the resulting mixture according to a suitable conversion technology. In this way it is possible to have available a wide range of materials endowed with improved properties in comparison with those obtained from the individual components of the mixtures.

The polyesters of the invention were characterized by determining:

| | |
|---|---|
| Melting point: | thermal differential analysis at a heating rate of 20° C./minute. |
| Technological properties: | |
| modulus | ASTM D 638 and D 412 |
| tensile strength | |
| elongation at break | |
| Shore hardness | ASTM D 2240 |
| contact angle: | determination by means of a 40 X grazing light microscope |
| friction coefficient | ASTM D 1894-73 |
| water absorption | ASTM D 570 - 24 hours. |

The test-pieces were prepared by compression molding, operating at temperature higher 30° C.–40° C. than the polymer melting point, the polymer having been previously dried at 100° C. under vacuum.

EXAMPLES

The following examples are given for merely illustrative purposes and are not to be considered as limitative of the invention.

EXAMPLE 1

120.6 g (0.62 mols) of dimethyl terephthalate (DMT), 89.4 g (0.99 mols) of 1,4-butandiol and 1.2 10$^{-3}$ mols of titanium tetraisopropylate (in an isopropanol solution) were charged into a tree-neck flash having a 0.5-liter volume, equipped with a stirrer, a dropping funnel and a column for the distillation of the reaction by-products.

Into the dropping funnel there were introduced 62 g (0.031 mols) of α,ω-bis-hydroxy-polyoxyperfluoroalkylene having an average molecular weight equal to 2000 (formula described at point 3), belonging to class I with A=OH; v=1; z=1).

The flask was repeatedly subjected to vacuum and nitrogen-filling cycles and was subsequently dipped into an oil bath previously heated to 200° C.

The reaction was conducted under stirring and in a nitrogen atmosphere, and the methanol distillation begun directly after melting of the mass.

After 30 minutes, when the distillation of the theoretical amount of methanol was concluded, the polyoxyperfluoroalkylene diol was added and the whole was allowed to react for 1 hour at 210° C.

The bath temperature was then brought to 250° C. while the pressure was gradually lowered to 0.1 torr.

Polycondensation was carried out for 2 hours, whereafter it was cooled to room temperature while simultaneously introducing nitrogen into the reaction flask until the atmospheric pressure was reached.

The fluorinated polyester, having the appearance of a light mass, exhibited the following characteristics:
melting point: 220° C.
Fluorine content: 18% by weight
Shore hardness D: 72
tensile strength: 540 kg/cm$^2$
elongation at break: 310%.

The oil- and water-repellency properties and the friction coefficient of the fluorinated polyester were compared with those of a polybutyleneterephthalate sample (check A).

| | Fluorinated polyester | Check A |
|---|---|---|
| contact angle with H$_2$O | 104 | 55 |
| contact angle with ligroin | 20 | complete wetting |
| contact angle with nitromethane | 55 | 36 |
| dynamic friction coefficient (μ) on steel | 0.15 | 0.33 |
| H$_2$O absorption (% by weight) | 0.08 | 0.65 |

EXAMPLE 1

Using the apparatus and the modalities described in example 1, a fluorinated thermoelastomeric polyester was prepared, which consisted of a rigid crystalline phase, a rubber-like amorphous hydrogenated phase, an amorphous fluorinated phase having a very low Tg.

The reaction mass consisted of DMT (48.5 g, equal to 0.25 mols), 1,4-butandiol (36 g, equal to 0.04 mols), polyoxytetramethylene glycol having an average molecular weight equal to 1000 (100 g equal to 0.1 mols) and Irganox 1098 ® (1 g) as antioxidant. In the second step there was added α,ω-bis-hydroxy-polyoxyperfluoroalkylene having an average molecular weight equal to 2000 and having the formula described at point 3), belonging to class I with A=OH; v=1; z=1 (12.5 g corresponding to 0.00625 moles). The catalyst is titanium tetraisopropylate (0.1% by moles referred to DMT).

After a 2-hours polycondensation, a high molecular weight fluorinated copolyester was obtained, exhibited the following properties:
melting point: 194° C.
Fluorine content: 4.6% by weight
Shore hardness D: 52
tensile yield strength (25% modulus): 132 kg/cm$^2$
tensile strength: 490 kg/cm$^2$
elongation at break: 480%.

Analogously with the preceding example, the fluorinated polymer properties were compared with those of a thermoelastomeric copolyether-ester not containing fluorine (check B).

| | Fluorinated thermoelastomeric polyester | Check B |
|---|---|---|
| contact angle with H$_2$O | 110 | 62 |
| contact angle with ligroin | 15 | complete |

| | Fluorinated thermoelastomeric polyester | Check B |
|---|---|---|
| contact angle with nitromethane | 59 | wetting 39 |
| dynamic friction coefficient ($\mu$) on steel | 0.20 | 0.45 |

EXAMPLE 3

776 g (4 mols) of dimethylterephthalate, 744 g (12 mols) of ethylene glycol, 0.7 g of manganese acetate (II) and 0.7 g of antimony oxide (III) were charged into a glass reactor having a 3 l volume, equipped with a stirrer, a dropping funnel and a column for the distillation of the reaction by-products.

Into the dropping funnel there were introduced 80 g (0.04 mols) of $\alpha,\omega$-bis-(methylcarboxylate)-polyoxyperfluoroalkylene having an average molecular weight equal to 2000 (formula described at point 3), belonging to class I, with A=COOCH$_3$, v=z 0).

The reactor was repeatedly subjected to vacuum cycles and was subsequently dipped into an oil bath heated to 180° C.

The mixture was stirred for 2 hours, during which the distillation of methanol toke place; after this period of time, the fluorinated diester was added and the whole was allowed to further react for 1 hour.

The bath temperature was then brought to 280° C. while simultaneously and progressively reducing the pressure to 0.1 mm Hg.

After a 2-hour polycondensation, during which the distillation of the ethylene glycol in excess occurred, it was cooled to room temperature.

The fluorinated polyester, (m.p.=250° C., Fluorine content=5% by weight), after grinding in rotary ball mill, was extruded at 290° C. by means of a laboratory flat-head extruder, was cooled to 25° C., longitudinally stretched at 95° C. to 300%, transversely stretched at 120° C. to 300% and subsequently treated at 215° C. for a few seconds to give a biaxially oriented film having a thickness of 100 $\mu$m.

The fluorinated polyester film exhibited improved surface properties with respect to a conventional polybutyleneterephthalate film.

In fact, the values of the contact angle with H$_2$O and of the dynamic friction coefficient on steel were equal to 103° and to 0.25, respectively, in comparison with 70° and 0.55 of a polybutyleneterephthalate film not containing fluorine.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A polyester having a block structure prepared through polycondensation reaction of the following compounds:

A) a hydrogenated diacid or diester or diacylchloride having the following general formula:

wherein Y and Y', equal to or different from each other, are halogen or OR', wherein R' is H or an alkyl radical having from 1 to 8 carbon atoms or an aryl radical having from 6 to 10 carbon atoms;

R$_2$ is a divalent radical having from 2 to 30 carbon atoms, selected from the class consisting of:
i) an alkylene radical;
ii) a fluorinated or non-fluorinated arylene radical;
iii) a cycloaliphatic or polycyclic, fluorinated or non-fluorinated, divalent radical;

B) a hydrogenated diol containing an alkylene radical having from 2 to 14 carbon atoms,;

C) a difunctional fluorinated compound having an average molecular weight from about 400 to 10,000, consisting of sequences of fluoropolyoxyalkylene units and having end groups of the following type:

$$—(CH_2)_v—(OCH_2CH_2)_z—A$$

wherein v and z are integers or zero, A is OH, in such case v being at least 1, or COY, Y being as defined hereinbefore at time A), said fluoro oxyalkylene units being selected from the following classes:

I) (C$_2$F$_4$O), (CF$_2$O), said units being randomly distributed along the fluoropolyoxyalkylene chain;

II) (C$_3$F$_6$O), (C$_2$F$_4$O), (CFXO) with S=—F or —CF$_3$, said units being randomly distributed along the fluoropolyoxyalkylene china;

III) —CH$_2$—CF$_2$—CF$_2$—O said units being linked to one another inside the fluoroalkylene chain as shown by the following structural formula:

$$—(O—CF_2—CF_2—CH_2)_p—O—R'-_f—O—(CH_2CF_2CF_2O)_q—$$

where R'$_f$ is a fluoroalkylene group, p and are integers, and p+q is at least 2;

IV)

said units being linked to one another inside the fluoropolyoxyalkylene chain as shown by the following structural formula:

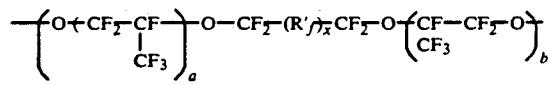

wherein R$_f$ is a fluoroalkylene group, x is 0 or 1, a and b are integers, and a+b is at least 2;

V) (CF$_2$CF$_2$O); and

VI) (CF$_2$CF$_2$CF$_2$O); said polyester being furthermore characterized in that the fluorinated compound of item C) is present in the final polyester production amount from 0.2% to 2.0% by moles based on the total moles of A)+B)+C).

2. Polyester according to claim 1, wherein in the polycondensation reaction is used also a hydrogenated polyoxyalkylene glycol having an average molecular weight from about 400 to 4,000, having the following general formula:

$$HO(C_dH_{2d}O)_gH$$

where $d=1-4$ and $g=6-70$, $C_dH_d$ being linear or having side chains.

3. The polyester according to claim 1, wherein the alkylene radical of item i) is selected from the class consisting of

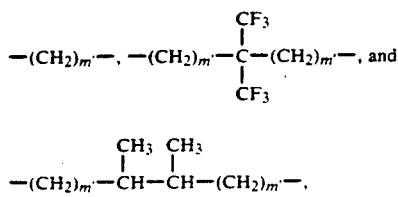

where m' is an integer from 2 to 20.

4. The polyester according to claim 1, wherein the arylene radical of item ii) is selected from the class consisting of para-phenylene, meta-phenylene, para-xylene, and meta-xylene.

5. The polyester according to claim 1, wherein the divalent radical of item iii) is selected from the class consisting of 1,4-cyclo-hexylene, 1,3-cyclohexylene, 2-methyl-1,4-cyclohexylene, 2-methyl-1,3-cyclohexylene, and darylemenmethane.

6. The polyester according to claim 1, wherein the difunctional fluorinated compound C) has an average molecular width from 500 to 5,000.

7. The polyester according to claim 2, wherein the polyoxyalkylene glycol has an average molecular width from 1,000 to 2,000.

8. The polyester according to claim 1, wherein v is zero or 1 and z is zero or an integer from 1 to 3.

9. The polyester according to claim 1, wherein the difunctional fluorinated compound C) is an aromatic dicarboxylic acid.

10. The polyester according to claim 1, wherein the difunctional fluorinated compound C) has the following formula:

$$A-(CH_2CH_2O)_z-(CH_2)_v-CF_2O-(C_2F_4O)_m-(CF_2O)-CF_2-(CH_2)_v-(OCH_2CH_2)_z-A$$

wherein v, z and A have the same meaning as defined in claim 1 and m and n are positive integers such that the molecular weight falls within the range 400–10,000.

* * * * *